US009604077B2

(12) United States Patent
Xing et al.

(10) Patent No.: US 9,604,077 B2
(45) Date of Patent: Mar. 28, 2017

(54) VISUALIZING RADIATION THERAPY BEAM IN REAL-TIME IN THE CONTEXT OF PATIENT'S ANATOMY

(71) Applicant: The Board of Trustees of the Leland Stanford Junior University, Palo Alto, CA (US)

(72) Inventors: Lei Xing, Palo Alto, CA (US); Dominik Jan Naczynski, San Diego, CA (US); Cesare Jenkins, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 14/739,896

(22) Filed: Jun. 15, 2015

(65) Prior Publication Data
US 2015/0360056 A1 Dec. 17, 2015

Related U.S. Application Data

(60) Provisional application No. 62/012,710, filed on Jun. 16, 2014.

(51) Int. Cl.
*G01T 1/161* (2006.01)
*A61N 5/10* (2006.01)

(52) U.S. Cl.
CPC .......... *A61N 5/1075* (2013.01); *A61N 5/1049* (2013.01); *A61N 2005/1059* (2013.01); *A61N 2005/1076* (2013.01)

(58) Field of Classification Search
CPC ...... A61N 5/10; A61N 5/1064; A61N 5/1081; A61N 2005/1052; A61N 5/107; G01T 1/161
See application file for complete search history.

(56) References Cited

U.S. PATENT DOCUMENTS

| 6,856,670 B2 * | 2/2005 | Hoheisel | H01L 27/14658 250/370.09 |
| 2010/0268074 A1 * | 10/2010 | Van Loef | A61B 6/032 600/431 |

OTHER PUBLICATIONS

Jung et al., Flexible Gd2O2S:Tb scintillators pixelated with polyethylene microstructures for digital x-ray image sensors, J. Micromech. Microeng. 19 (2009).

(Continued)

*Primary Examiner* — David Porta
*Assistant Examiner* — Faye Boosalis
(74) *Attorney, Agent, or Firm* — Lumen Patent Firm

(57) ABSTRACT

A method of real-time radiotherapy beam visualization is provided that includes disposing a free-form flexible scintillating sheet on a subject of interest, irradiating the subject of interest with a source of ionizing radiation, where the free-forming flexible scintillating sheet emits light when irradiated by the therapeutic photon beam, collecting the emitted light and collecting ambient light reflected from the subject of interest and surrounding objects using a camera, where the collected light is converted to image data by the camera, where the image data is communicated to an appropriately programmed computer, and processing the image data to determine beam characteristics and the characteristics of the subject of interest, using the appropriately programmed computer, where the beam characteristics and the characteristics of the subject of interest are displayed in real-time to a machine operator enabling real-time verification of treatment delivery.

24 Claims, 11 Drawing Sheets

(56) References Cited

OTHER PUBLICATIONS

Zaman et al. Scintillating Balloon-Enabled Fiber-Optic System for Radionuclide Imaging of Atherosclerotic Plaques, The Journal of Nuclear Medicine • vol. 56 • No. 5 • May 2015.

* cited by examiner

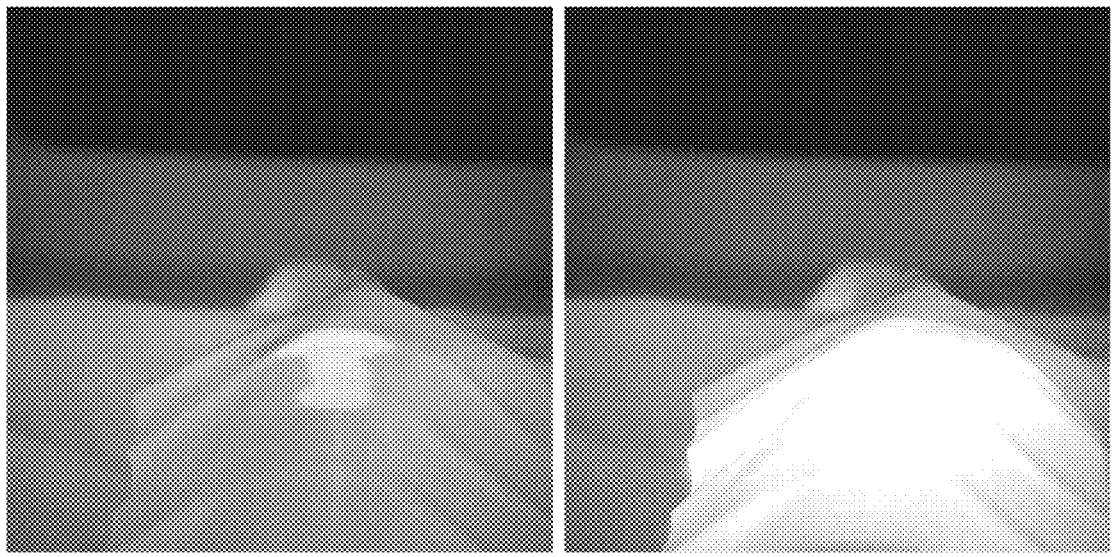
*FIG. 8A*  *FIG. 8B*
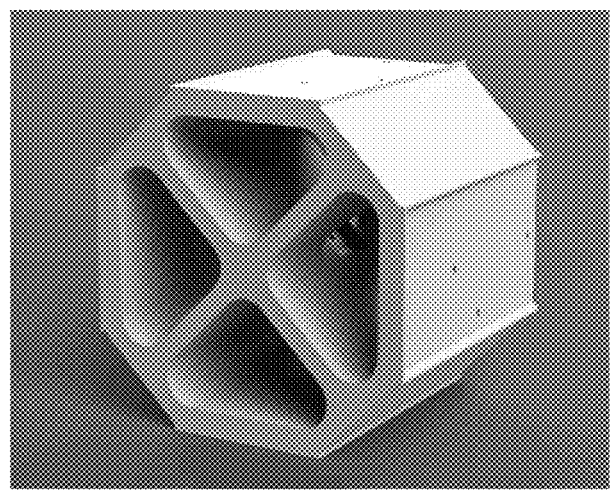
*FIG. 9*

VISUALIZING RADIATION THERAPY BEAM IN REAL-TIME IN THE CONTEXT OF PATIENT'S ANATOMY

CROSS-REFERENCE TO RELATED APPLICATIONS

This application claims priority from U.S. Provisional Patent Application 62/012,710 filed Jun. 16, 2014, which is incorporated herein by reference.

FIELD OF THE INVENTION

The present invention relates generally to radiotherapy. More particularly, the invention relates to a system and method of visualizing a radiotherapy treatment beam entrance or exit relative to the patient.

BACKGROUND OF THE INVENTION

External beam radiation therapy (EBRT) is one of the most commonly used treatments for numerous cancer types. In 2010, approximately 470,000 patients underwent radiation therapy (RT) in the US alone. Depending on their individual treatment plan, these patients may undergo between 1 and 70 separate RT visits over the course of several weeks. Although most RT treatments are performed accurately, accidents from equipment faults, failures in quality assurance methodologies, and errors during operation represent an unacceptable risk for both patients and healthcare providers. Recent reports indicate that between 0.6 and 4.7 incidents per 100 radiation therapy visits have been reported to occur even in advanced oncology centers operating with modern equipment and trained staff. However, these numbers may be grossly underestimated, as it is also widely recognized that many incidents remain unreported during RT. A significant number of these incidents occur during the delivery of RT and can result in underdosing or overdosing patients, irradiating healthy tissue, or, at worst, patient death. As EBRT techniques continue to increase in complexity, and with the increased use of stereotactic body radiotherapy (SBRT) and hypofractionation, there is a clear and growing need for a monitoring and validation methodology that enables clinicians to have greater confidence that they are delivering the planned dose where and how it was intended.

The standard of care for RT involves multiple steps, such as simulation, treatment planning, plan verification, patient setup, and treatment delivery. While numerous methods [e.g., in room lasers, tattoos on patient skin, mega- and kilovoltage (MV, kV) imaging, pretreatment dosimetry phantom studies, etc.] have been developed to ensure the fidelity of treatment delivery, there are no technologies currently available that are capable of fully monitoring treatment in the context of the patient's anatomy as it is being delivered.

In current practice, onboard MV electronic portal imaging (EPID) is utilized for monitoring the RT beam after it exits the patient. However, due to a lack of soft tissue contrast and multileaf collimator (MLC) blockage of the field of view, the available anatomic references provided by the approach are limited to bony anatomy or implanted fiducial markers that lie within the beam's eye view making the interpretation of the data nontrivial. More recently the potential of Cherenkov emission as a means of visualizing therapy in real time has been demonstrated. Also proposed was a method of utilizing air scintillation to visualize the radiation beam. While both seek to visualize therapeutic beam delivery, the signals generated are at least three orders of magnitude smaller than typical room lights. Thus, these techniques require long exposure times in darkened rooms or complex, expensive imaging setups to obtain usable measurements.

This poses a challenge to practical application. Therefore, the ability to visualize the position, shape, and intensity of the radiation beam as it passes through the patient in real time is not yet available in clinical practice.

What is needed is an imaging approach that can be readily implemented into existing RT treatment rooms and provide a means of monitoring beam shape, intensity and general location in real time.

Additionally, in the radiation therapy space, a great deal of effort is expended upon ensuring that medical sources of ionizing radiation operate properly. This is generally referred to as Quality Assurance (QA) and generally involves testing several aspects of the performance of the radiation therapy machines at regular intervals. Often these tests are time-consuming, tedious, and prone to operator error. Similar to the needs in monitoring therapy in real-time, there exists the need to perform quality assurance measurements with high temporal resolution and in an automated fashion.

SUMMARY OF THE INVENTION

To address the needs in the art, a method of real-time radiotherapy beam visualization is provided that includes disposing a free-form flexible scintillating sheet on a subject of interest, irradiating the subject of interest with a source of ionizing radiation, where the free-forming flexible scintillating sheet emits light when irradiated by the source of ionizing radiation, collecting the emitted light, collecting ambient light, or collecting emitted light and ambient light reflected from the subject of interest and surrounding objects using a camera, where the collected light is converted to image data by the camera, where the image data is communicated to an appropriately programmed computer, or directly to a viewing screen, and processing the image data to determine beam characteristics and characteristics of the subject of interest, using the appropriately programmed computer, where the beam characteristics, the characteristics of the subject of interest, or the beam characteristics and the characteristics of the subject of interest are displayed in real-time to a machine operator enabling real-time assessment of treatment delivery or stored on recordable media for later review.

According to one aspect of the invention, the free-form flexible scintillating sheet includes a scintillating powder mixed with silicone. In one aspect the scintillating powder includes GdO2S:Tb, or GdO2s:Eu.

In another aspect of the invention, the source of ionizing radiation includes a medical linear accelerator or a photon beam.

In a further aspect of the invention, the camera includes a stereo-pair of the cameras, where image data processing includes a 3D scene reconstruction, or 3D localization of points within the image data. In one aspect the camera includes a digital camera.

In yet another aspect of the invention, the image data is compared with treatment planning data to determine an efficacy of treatment delivery. In one aspect, the comparison of the image data includes comparing an image of the subject of interest and the beam characteristics with a corresponding treatment planning software image of the subject of interest and a corresponding treatment planning software image of the beam characteristics. In another aspect, a relative location of the beam characteristics and patient anatomical landmarks are determined during data processing and compared with relative locations of corresponding elements in a treatment plan.

According to one aspect of the invention, data presented to an observer includes a value and tolerance for a deviation of the beam characteristics relative to values from a treatment plan, where the beam characteristics comprise a beam location relative to anatomical markers, beam intensity, or beam flatness. In one aspect, the appropriately programmed computer determines whether calculated data is consistent with a treatment plan, where the appropriately programmed halts a treatment if a disparity is detected.

According to another aspect of the invention, the collected image data is processed to determine an efficacy of the ionizing radiation source.

In a further aspect of the invention, the processed image data is used to update the treatment plan in real time.

In yet another aspect of the invention, the processed image data is used to update a treatment plan prior to a subsequent treatment.

In one aspect of the invention, the image data is stored and may be retrieved at a future time to review treatment delivery.

According to one aspect of the invention, the camera includes a bandpass filter, where the bandpass filter passes an emission band of emission from the scintillating material.

In a further aspect of the invention, the camera is synchronized to the source of ionizing radiation to enable acquisition of light only during a specified period of time, where the specified period of time corresponding to the production of the ionizing radiation or a period of time following the production of ionizing radiation.

In another aspect of the invention, the appropriately programmed computer includes an image processing algorithm, where the image processing algorithm includes the image processing steps of background subtraction, outlier removal, calculating a contract-to-noise ratio and pixel values, where the contrast-to-noise ratio and the pixel values are output, transformation and cropping an image with the determined contrast-to-noise ratio and the pixel values, equalization of a histogram, applying an adaptive threshold, extracting and filtering image contours, determining Hough lines, and outputting a field center calculation and determined average lines of a collimator location.

According to another embodiment of the invention, a method of radiation therapy quality assurance assessment is provided that includes coating a phantom with a scintillating material that conforms to the external shape of the phantom, and irradiating the coated phantom, using a therapeutic beam from a medical source of ionizing radiation, where the scintillating material emits light when exposed to the source of ionizing radiation, where the emitted light is collected by a camera, where the camera forms image data, where the image data is sent to an appropriately programmed computer, where the data is processed to determine characteristics of the beam and to determine an accuracy of machine operation for output to an operator.

According to one aspect of the current embodiment, the collected image data is used to determine acceleration, velocity, accuracy and repeatability of mechanical motions of the source of ionizing radiation. In one aspect, the medical source of ionizing radiation includes a linear accelerator where evaluated mechanical motions are selected from the group consisting of motions of the gantry, collimator, collimators, source and couch. In a further aspect, the source of radiation comprises a radioactive seed, where the evaluated motions include the motions of the speed.

In a further aspect of the current embodiment, the collected image data is used to determine radiation source properties that include fluence, flatness, or energy.

In yet another aspect of the current embodiment, the phantom contains radio-opaque markers, and where the images of the radio-opaque markers are formed using a medical imaging system, where the alignment of the radiation source to the medical imaging system is assessed by processing of the images.

BRIEF DESCRIPTION OF THE DRAWINGS

FIGS. 7A-7C show an entry beam profile as the gantry moves from approximately 0°-30°, and FIGS. 7D-7F show an exit beam profile as the gantry moves from approximately 70°-90°, according to embodiments of the current invention.

FIGS. 8A-8B show RT-BV images of a field being delivered with the MLC leaves properly in place (FIG. 8A) and fully retracted (FIG. 8B).

FIG. 9 shows a computer rendering of a phantom used in the exemplary system QA, according to one embodiment of the invention.

(FIG. 10B) initial transformation of the image based on the pose of the phantom in the image; (FIG. 10C) the image transformed to account for location and orientation of the phantom relative to light-field, where the extracted location of the light field crosshairs shown in bold lines; (FIG. 10D) the transformed image used to extract the locations of the lasers, according to embodiments of the current invention.

DETAILED DESCRIPTION

Figure 1:
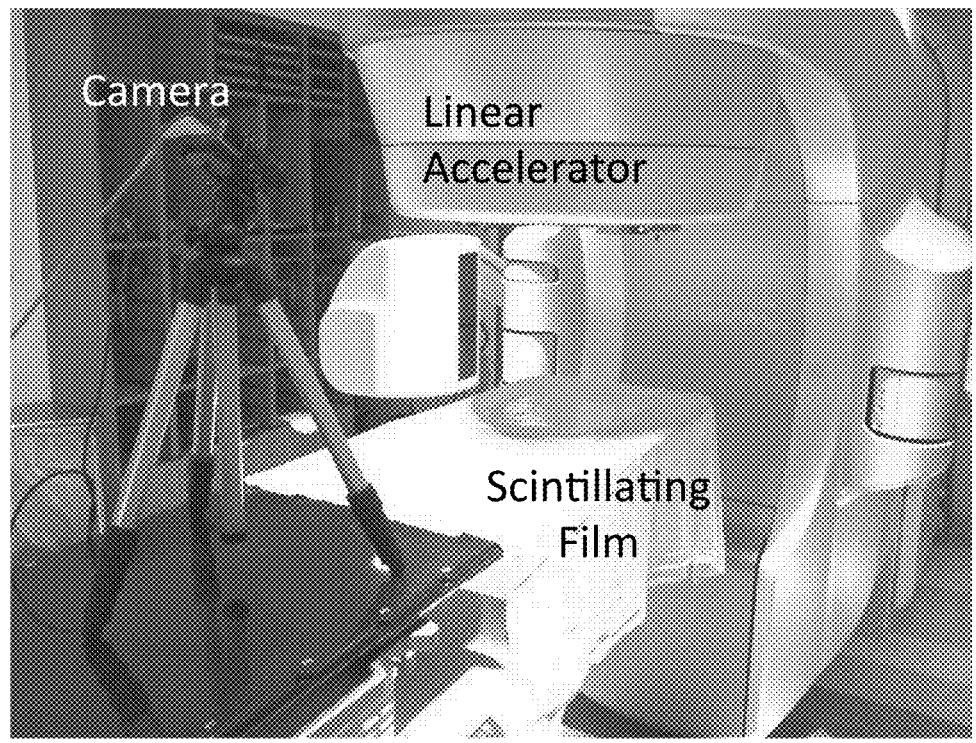
FIG. 1 shows a photograph of an imaging setup, according to one embodiment of the invention.

The current invention is a real-time beam visualization (RT-BV) system and method that includes of a flexible scintillating film and a camera. In one embodiment, the film is placed on a patient's skin such that it will emit an optical signal when the beam passes through it. The camera is arranged such that it can image the emitted signal as well as the surrounding patient surface anatomy. An exemplary embodiment is provided herein that includes characterization and integration of the RT-BV system for application in a RT treatment room. An image-processing algorithm was developed to demonstrate how the data from the RT-BV system could be analyzed and interpreted to provide quantitative treatment verification, as well as to aid in assessing the quality of the data from the system.

According to one embodiment, a method of real-time radiotherapy beam visualization is provided that includes disposing a free-form flexible scintillating sheet on a subject of interest, irradiating the subject of interest with a source of ionizing radiation, where the free-forming flexible scintillating sheet emits light when irradiated by the therapeutic photon beam, collecting the emitted light and collecting ambient light reflected from the subject of interest and surrounding objects using a digital camera, where the collected light is converted to image data by the digital camera, where the image data is communicated to an appropriately programmed computer, and processing the image data to determine a beam profile and the characteristics of the subject of interest, using the appropriately programmed computer, where the beam profile and the characteristics of the subject of interest are displayed in real-time to a machine operator enabling real-time verification of treatment delivery.

In yet another aspect of the invention, the digital camera is synchronized to the source of ionizing radiation to enable acquisition of light only during a specified period of time, where the specified period of time corresponding to the production of the ionizing radiation or a period of time following the production of ionizing radiation.

Turning now to X-ray scintillation and room light spectra, as one approach of rejecting ambient light, the emission spectrum of the lights in the radiation therapy room and the scintillating portion of the film are examined. In this example, spectra of the scintillating material were acquired using a monochromator (Acton SP2150, Princeton Instruments, Trenton, N.J.) in conjunction with a Princeton Instruments EMCCD camera (Pro-EM). Loose Gd2O2S:Tb (GOS) powder was placed in a clear, plastic cuvette and irradiated with a mini x-ray source (Amptek, Bedford, Mass.) operating at 50 kV and 80 µA. The emission spectrum of the room lights was measured using a fiber-optic spectrometer (Ocean Optics, Dunedin, Fla.). In one aspect the scintillating powder can be GdO2s:Eu.

Regarding the flexible scintillating film, the desirable features of a scintillation film to be placed on the patient include sufficient signal generation, minimal dose attenuation, and sufficient flexibility to conform to anatomy. In this example, scintillating films were prepared by mixing GOS scintillating phosphor powder and a silicone elastomer in a 1:1 mass ratio. The resulting mixture was cast on a level surface at a thickness of 0.8 mm and allowed to cure at room temperature.

In the imaging setup of this example, the imaging setup, shown in FIG. 1, includes a 2048×2048 pixel CMOS digital camera equipped with a 50 mm lens and a band-pass filter, where according to one embodiment, the bandpass filter passes an emission band of emission from the scintillating material.

The camera was placed 100 cm inferior and 50 cm anterior of isocenter. The halogen lights in the treatment room were set to maximum intensity for all image acquisition. The camera was selected primarily based on its resolution, bandwidth, and cost with secondary consideration given to noise characteristics. All images were acquired with a 42 ms integration time with the gain of the camera set to its minimum value. At this integration time, a frame rate of 23 frames per second (fps) is achievable. When imaging static fields, images were acquired at a rate of 5 fps. In general, each set of data included of 10 images (spanning a 2 s interval). Images were analyzed using ImageJ 1.47v (National Institute of Health, Bethesda, Md.), MATLAB 7.8.0 (The MathWorks, Inc., Natick, Mass.), and OpenCV.

For characterization of the basic system, radiation was delivered using Varian EX and TrueBeam medical linear accelerators (LINAC) (Varian Medical Systems, Palo Alto, Calif.). Beam energies between 6 and 15 MV were investigated with dose rates ranging between 200 and 600 MU/min. Square fields were used for general system characterization.

In order to assess the dose attenuation of the sheet, a Farmer chamber was placed inside a solid water phantom at an approximate depth of 6 cm and connected to an electrometer. Identical exposures were delivered with and without the film in place. The integrated charge was recorded after each delivery.

In order to assess the effect of the sheet on surface dose, a parallel plate ion chamber (Exradin A10, Standard Imaging, Inc., Middleton, Wis.) was placed at the surface of a 10 cm slab of solid water. 200 MU was delivered with a 600 MU/min dose rate for both 6 and 15 MV beam energies with the surface of the chamber located at 100 cm SSD. The procedure was repeated with the scintillating film placed over the ion chamber. The film was then removed and a solid water layer of 1.5 and 3 cm, for 6 and 15 MV beams, respectively, was placed over the chamber. The couch was adjusted to maintain a SSD of 100 cm to the top of the solid water and the exposure was repeated. The percent-depth-dose (PDD) was calculated at the surface and beneath the film. The calculated PDD was corrected for chamber over-response.

For MLC visualization and simulated accidental refraction, in order to verify the resolution and beam shape fidelity of the system, complex MLC shaped fields were delivered and imaged simultaneously with the RT-BV system and a Varian EPID portal imaging system. The test field was designed with alternating leaves opened to distances of 0.1, 0.2, 0.3, 0.5, 0.8, 1, 2, 3, 5, and 8 cm in both the lower left and upper right quadrants. The lower portion of the field had unopened leaves completely extended while the upper portion included a 2 cm gap. Finally, a full VMAT plan was imaged as it was delivered to an anthropomorphic phantom.

To evaluate the capabilities of the imaging platform for detecting gross abnormalities in treatment delivery, a proof-of-concept study was conducted simulating an accidental MLC retraction. The film was placed on a small cylindrical object and allowed to deform as necessary to conform to its shape. An example field of 6 MV was delivered at 600 MU/min. The MLC was then fully retracted and the field was imaged with only the jaws in place.

In a further embodiment of the invention, the appropriately programmed computer includes an image processing algorithm, where the image processing algorithm includes the image processing steps of background subtraction, outlier removal, calculating a contract-to-noise ratio and pixel values, where the contract-to-noise ratio and the pixel values are output, transformation and cropping an image with the determined contract-to-noise ratio and the pixel values, equalization of a histogram, applying an adaptive threshold, extracting and filtering image contours, determining Hough lines, and outputting a field center calculation and determined average lines of a collimator location.

Figure 2:
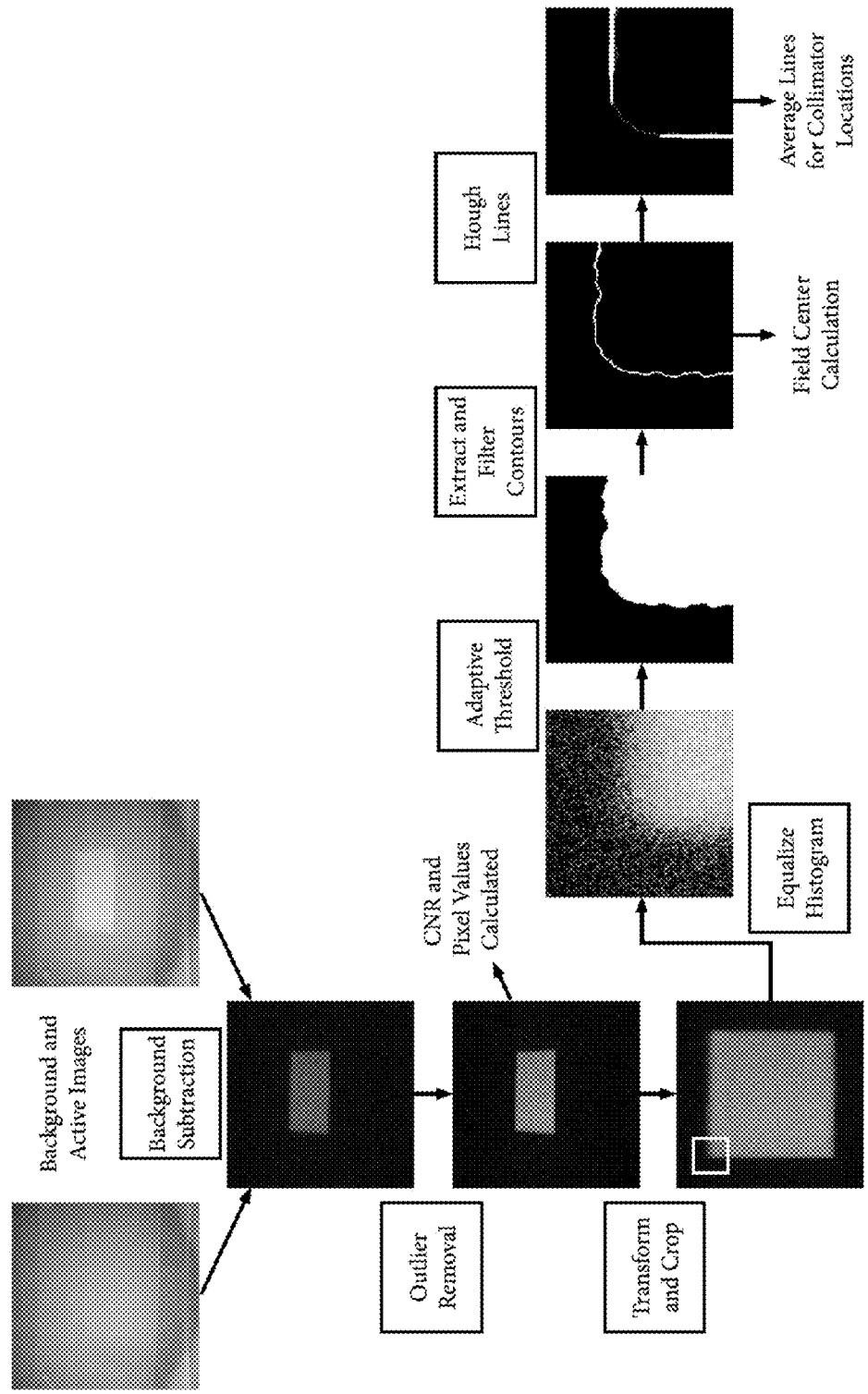
FIG. 2 shows a graphical overview of the image processing algorithm utilized, according to one embodiment of the invention.

Turning now to the image processing algorithm, an image processing algorithm was designed to robustly identify and locate the beam within each image in a beam-on dataset. FIG. 2 shows a graphical overview of the image processing algorithm utilized. For each dataset, a set of 10 background images were captured both before and after the acquisition of beam-on images. These background images were averaged together to form a single background image. The background image was then subtracted from each beam-on image in the dataset. Bright outliers, caused by stray x-rays interacting with the camera sensor, were removed from the images by comparing pixel values with the median value of a neighborhood around each pixel. Pixels whose values exceed this median by more than a specified amount (threshold) are set to this median value while other pixels remain unchanged.

Contrast-to-noise ratios (CNRs) were calculated by taking the average pixel intensity of a region of interest (ROI) within the bright region of the processed image and dividing it by the standard deviation (SD) of the pixel intensity values within a ROI of the same size in a background area of the processed images. A projective transformation was used to correct for the distortion introduced due to the angled positioning of the camera. The transformation was found by extracting the four corners of a square field of known dimensions in the image space. Corresponding points in real-world coordinates were determined from the field size and location. The same transformation matrix was then applied to each image from that imaging setup.

Images of 10×10 cm fields were visualized with a range of collimator settings. These images were background subtracted, outliers removed, transformed, and cropped. Next, image processing was used to extract the field profile from the surrounding image.

A threshold value was identified that would best segment the resulting images. A binarization based on this value was applied to the images. Connected components were extracted from the binary images. The contours were then filtered by size to identify one that corresponds to the beam profile. The center of the field was calculated from the mass center of the pixels along the identified contour. The outline of the contour was then fit for straight lines using a probabilistic Hough transform. Lines were grouped according to their angle and location within the image to identify each of the four collimators. An average location for each group was calculated from $$c_d = \frac{\sum \bar{d} l e^{-|\delta|}}{\sum l e^{-|\delta|}}$$

where $c_d$ is the reported collimator location, $\bar{d}$ is the average pixel coordinate for each line (in the direction of interest), l is the length of the line, and $\delta$ is the angular deviation of the line from the ideal collimator direction (i.e., 90° for the x-collimators).

The parameters for each step were adjusted to minimize the measurement variation within each set while applying the same parameters across all images.

Figure 3:
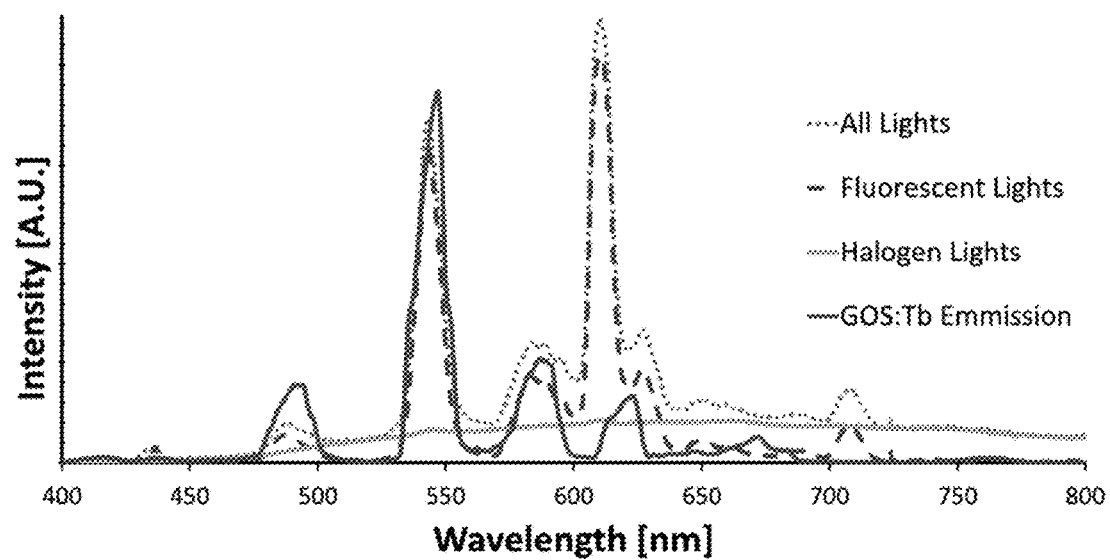
FIG. 3 shows the emission spectrum for the GOS that was used for the scintillating sheet, according to one embodiment of the invention.

The exemplary system performance is discussed as follows. Scintillating films were measured to be approximately 0.8 mm in thickness, highly durable, and flexible. Slight localized variations of ±0.1 mm in sheet thickness were detected with physical measurements made with digital calipers. The GOS was homogeneously distributed within the silicone. The emission spectrum for the GOS that was used for the scintillating sheet is shown in FIG. 3. The results reveal that the scintillator has a very strong emission near 550 nm, with additional peaks nearby. FIG. 3 also shows the emission spectrum for the lights in the LINAC room. There are two types of lights in the room, fluorescent and halogen. The fluorescent lights exhibit peaks characteristic of the dopants used in the bulb while the halogen lights exhibit a smooth distribution across all visible wavelengths.

Figure 4:
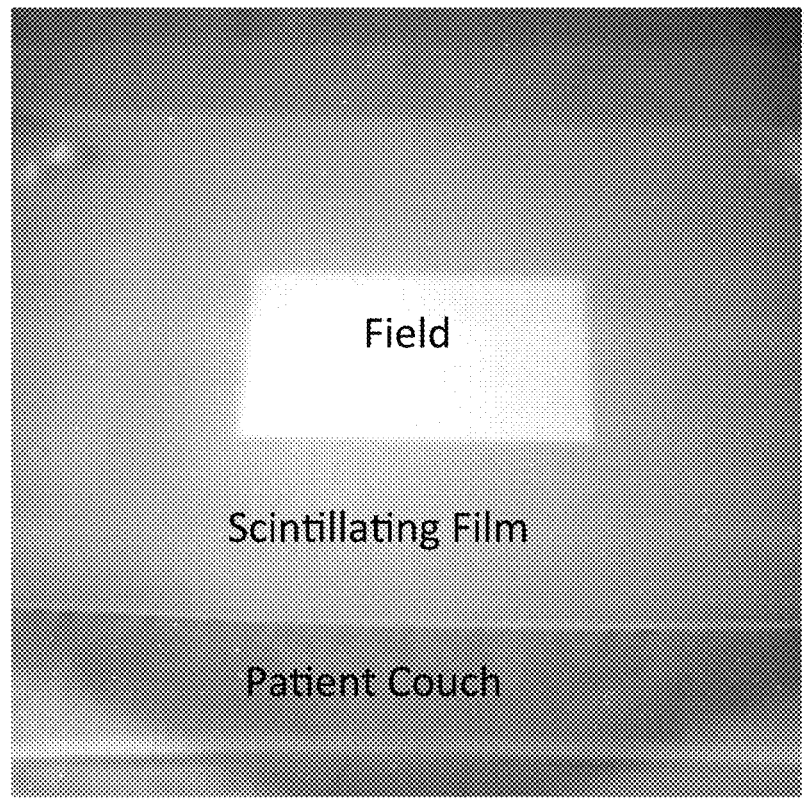
FIG. 4 shows an unprocessed image of the scintillating film being exposed to a 10×10 cm 6 MV 600 MU/min field, where both the film and the field are clearly visible, according to one embodiment of the invention.
Figure 5:
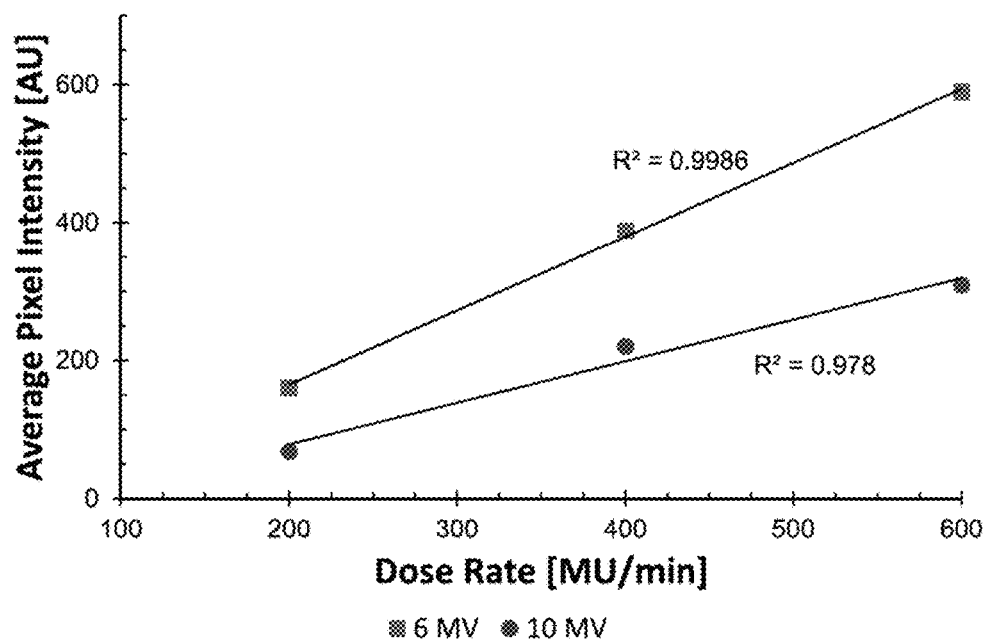
FIG. 5 shows light intensity was linearly correlated with dose rate and decreased with beam energy, where error bars for each data point fell within the marker.

An unprocessed image of the film being exposed to a 10×10 cm square field is presented in FIG. 4. The processed images of 10×10 cm fields for 6 and 10 MV beams with dose rates between 200 and 600 MU/min revealed clear field boundaries and reasonable uniformity across the field. For beams delivered at a higher dose rate, the penumbra of the beam can also be observed. A plot of average pixel value against dose rate for two different beam energies is presented in FIG. 5. Pixel intensity values increased with dose rate in a highly linear (R2>0.97) fashion. The beam energy affects the slope of this linear relation. The average CNR for sets of 10 images at each beam setting is reported in Table 1. The standard deviation is also presented offering insight into the variation in measurements.

TABLE 1

CNR (SD) for 10 × 10 cm fields at various beam settings.

| Beam energy (MV) | Dose rate (MU/min) | | |
| --- | --- | --- | --- |
| | 200 | 400 | 600 |
| 6 | 4.0 (0.11) | 9.4 (0.38) | 18.7 (0.82) |
| 10 | 1.9 (0.12) | 4.9 (0.16) | 8.6 (0.32) |

The dose attenuation due to the scintillating film in the fall off region was found to be less than 0.6% (Table 2). PDD measurements at the surface with and without the film in place yielded 60% and 17% for a 6 MV beam and 41% and 12% for a 15 MV beam. With the optimization of the film and optical imaging system, the thickness of the film can be greatly decreased, leading to much improved surface dosimetry.

TABLE 2

Dose attenuation caused by the imaging film in the falloff region.

| Beam energy (MV) | Integrated charge (nC) | | |
| --- | --- | --- | --- |
| | No sheet | With sheet | % Change |
| 6 | 38.18 | 37.95 | −0.61 |
| 15 | 43.59 | 43.36 | −0.54 |

Figure 6A:
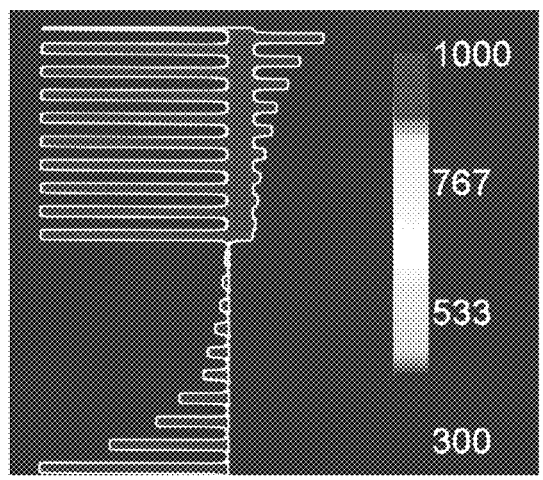
FIGS. 6A-6B show images of a test field imaged simultaneously with an EPID portal imaging system (FIG. 6A) and the RT-BV system (FIG. 6B), according to one embodiment of the current invention.
Figure 6B:
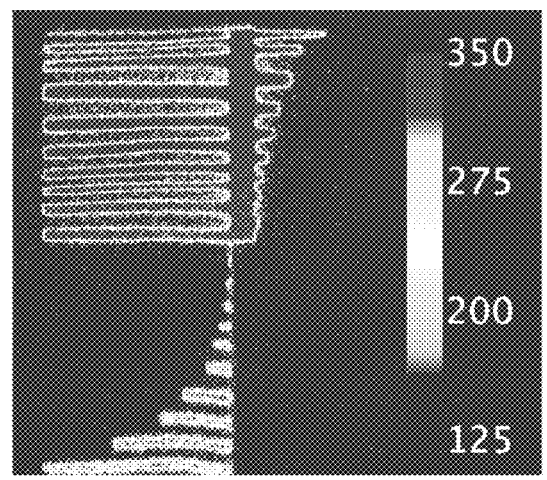
Figure 7C:
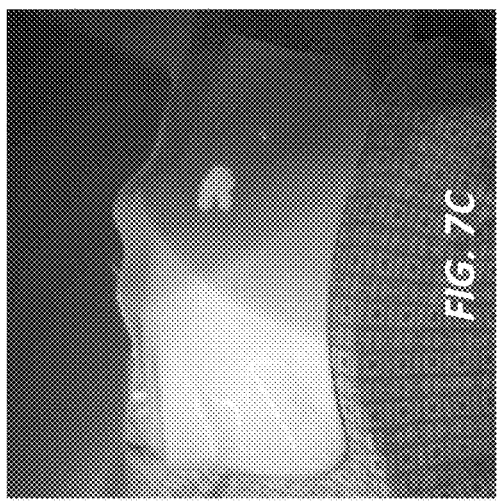
FIGS. 7A-7F show sequential images of a VMAT plan being delivered to an anthropomorphic phantom, where
Figure 7F:
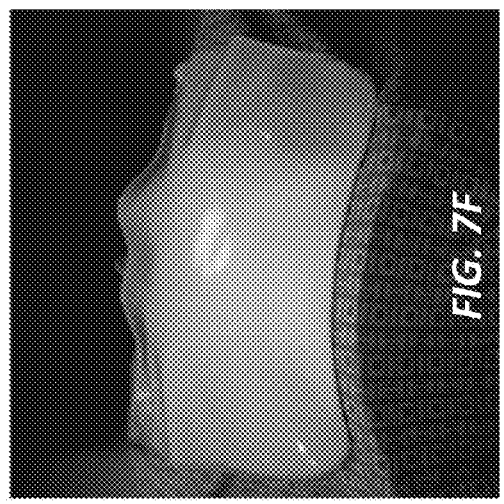
Figure 7B:
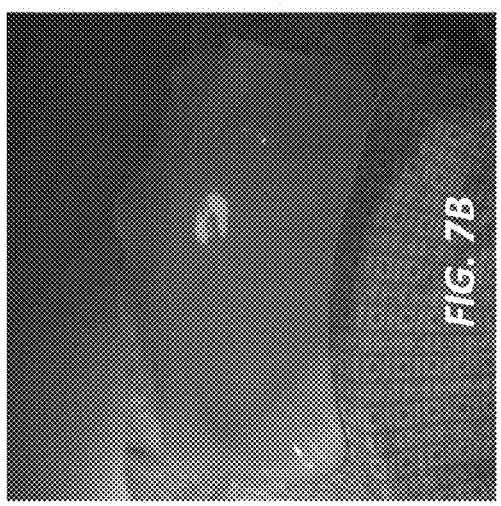
Figure 7E:
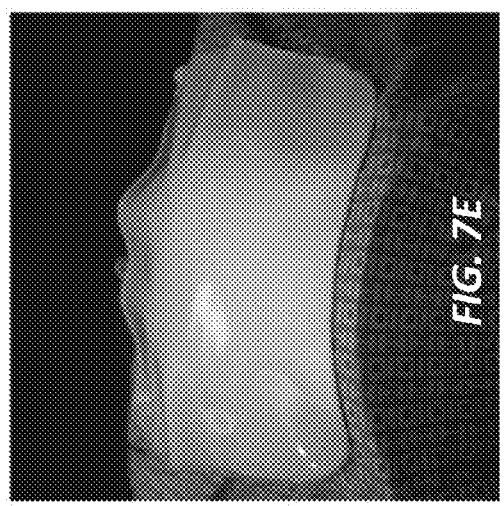
Figure 7A:
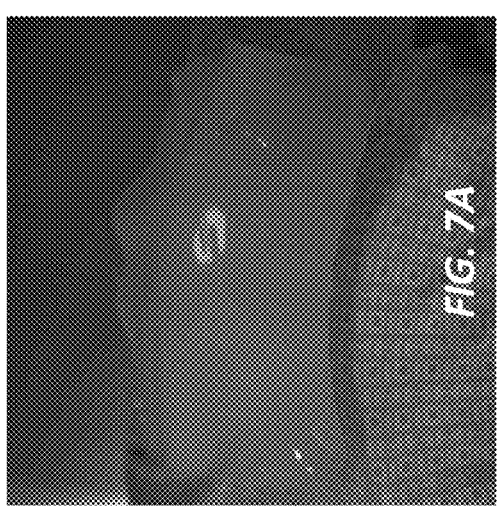
Figure 7D:
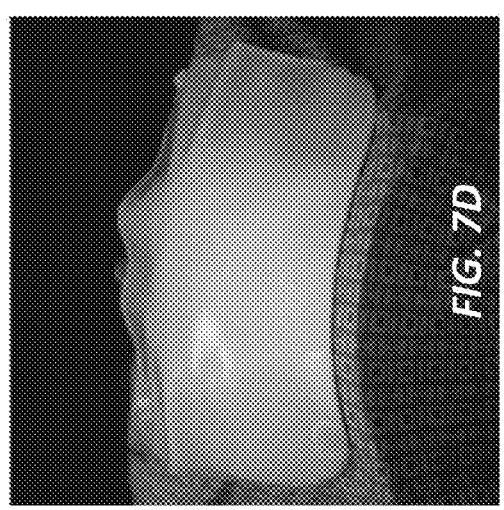

For MLC visualization, FIGS. 6A-6B show the result of a simultaneous acquisition with an EPID portal imager and the presented system for a complex test field. All features are discernable, including those created by 1 mm leaf movements near the center of the field. A discernable difference is also observable between features created by leaf locations that vary by 1 mm. Several frames from the imaged VMAT plan are presented in FIGS. 7A-7F. The field, sheet, and phantom are all visible.

FIGS. 8A-8B show two images from the treatment room where a simulated throat cancer patient is being treated with an IMRT field. A marked difference is easily observed between the field that is being delivered with the MLCs properly in place and the one that is being delivered with the MLCs fully retracted.

Turning now to the image processing algorithm performance, the results of the collimator localization algorithm were obtained, where the programmed machine locations for each corner and the center of a square 10×10 cm field were collected in addition to the algorithm estimation. In general, the algorithm was able to locate the collimators well within the 1 mm machine tolerance. The average deviation between machine and estimated locations was 0.5 mm. The maximum deviation was 2 mm.

The current invention provides an approach that permits real-time RT visualization under typical treatment room lighting conditions. Real-time beam tracking offers several advantages for RT delivery, including the ability to monitor beam position and shape as it enters or exits a patient during treatment. One embodiment of the current invention utilizes a low-cost CMOS camera positioned near the treatment bed to detect the beam as it interacts with a thin, scintillating film positioned on the patient. The film includes a GOS scintillating powder embedded within silicon allowing the scintillating material to deform to the unique contours of each treatment area. The GOS scintillating powder was selected due to its high light yield, enabling the use of inexpensive cameras and minimizing dose attenuation.

While the measured thickness of the exemplary prototype film was 0.8 mm, a critical parameter for understanding the effect on dose is the water equivalent thickness of the film. The cured silicone elastomer has a density of 1.03 g/cm$^3$ while the GOS has a density of 7.34 g/cm$^3$. An equal mass mixture is expected to have a density of 1.8 g/cm$^3$. Using a mass density based scaling, the expected water equivalent thickness of the film would be 1.44 mm. An analytical estimate and CT image analysis of the film suggested that the relative electron density of the film was 1.7-2 times that of water. Therefore, the water equivalent thickness of the film would be 1.6 mm. The increased surface dose observed with the sheet in place corresponds to a water depth of approximately 2 mm. The increase in surface dose needs to be carefully considered prior to clinical implementation, but we expect that by reducing the thickness and/or scintillator concentration in the film, the equivalent thickness can be reduced to half of its current value.

Since both GOS and the typical fluorescent lighting found in treatment rooms have a strong emission peak around 550 nm, the two light sources cannot be separated using traditional optical filtering methods. However, the smooth distribution of the halogen lights enables rejection of a significant amount of light in the measurements while maintaining a high level of illumination in the room. This motivated the selection of a 546 nm band-pass filter and the chosen room illumination scheme. It should also be noted that general clinical practice is usually to use only halogen lights during treatment. Once the room lights and optical filter had been selected, the image acquisition parameters were adjusted to maximize the CNR of the field, maintain a clear bright-field view of the treatment room (see FIG. 4), and obtain a reasonable frame rate for real-time monitoring. In order to achieve these goals the camera gain was set to a minimum and the integration time was increased to the maximum that enabled a desired frame rate. The quality of the images could be further increased by extending the integration time, at the cost of a reduced frame rate.

The maintenance of a clear bright-field image enables the extraction of information about the beam and the treatment room and/or patient from the same image, thereby enabling simultaneous tracking of both the patient and the field in the same reference frame. CNR was selected as the figure of merit because it best represents the ability of the system to separate the beam from the background image. While CNR is reduced at higher energies and lower dose rates (Table 1), temporal or spatial binning could be applied if necessary.

Average pixel intensity values increase linearly with dose rate and decrease with beam energy. The linearity with dose rate is expected since light output of GOS and some GOS composite materials is known to be linear with absorbed dose. The decrease in the slope of the signal vs dose-rate relationship with increasing beam energy is consistent with the reduction, at higher energies, in the rate at which dose is deposited at the surface (FIG. 6). It is interesting to point out that the ratio of light signals generated by the 6 and 10 MV photons remains roughly constant as the dose rate increases, indicating that the light production of the phosphor sheet depends little on beam energy. While further experiments are necessary to establish the dosimetry characteristics and dependencies of the system, the observed linearity is consistent with expected surface dose.

FIGS. 6A-6B show that the resolution of the system is sufficient to distinguish individual MLC leaves as well as 1 mm movements therein. There is excellent overall agreement between the image acquired with the EPID portal imager and the system. The small amounts of distortion that appeared in the image were due to the fact that the film was not perfectly flat on the couch during imaging. While these distortions are detrimental to imaging the beam in a flat orientation, it demonstrates that the film is capable of representing the beam profile as it is modulated by the contours of a patient's anatomy. FIG. 8A-8B demonstrates the potential utility of this fact as a gross error is immediately recognizable as it is viewed within the context of the surrounding surface shape of the patient. In this context, the deformation of the film to the patient's skin is of critical importance as any deviation between the film and the patient's skin will degrade the fidelity of the data collected by the system and, as with bolus, potentially introduce dose abnormalities. Future iterations of the sheet could utilize a silicone elastomer of lower durometer enabling greater flexibility.

The localization algorithm was able to properly identify the collimator settings in the acquired images. The reported locations are generally consistent with the LINAC values. Due to the use of an adaptive thresholding technique, the algorithm was able to provide consistent results even with variations in room lighting during delivery. The presented localization algorithm was developed to evaluate the quality and consistency of data generated by the system. As such, the exemplary algorithm was designed to evaluate square fields when the film is placed flat on the couch.

The RT-BV system is capable of obtaining images with sufficient CNR in the presence of full room illumination regardless of beam settings. The RT-BV system offers the ability to modulate the type and concentration of scintillator used in the film as well as the thickness and physical properties thereof. While placing the film in the path of the beam does introduce a perturbation to the radiation beam and an increase in surface dose, it enables the system to obtain images with an inexpensive imaging setup and provides additional flexibility in developing therapy monitoring systems that can visualize the beam in the context of local patient anatomy.

Imaging approaches based on air scintillation or Cherenkov radiation also offer the ability to visualize the beam. These techniques enjoy the advantage of not perturbing the treatment beam but generally require much more advanced imaging setups and image processing. EPID based techniques measure the beam aperture exiting the patient, but interpreting the data relative to patient anatomy is nontrivial. The current invention enables high-resolution images of the beam in a context that is immediately interpretable. It also offers the potential for gathering beam dosimetry data at beam entry based on the intensity of emitted optical signal from the film. A combined use of EPID and the RT-BV system may be valuable and allow us to harness the strengths of both systems to provide a complete view of therapy.

In a further embodiment of the invention, a flexible scintillating sheet is placed on a patient, and a closed circuit TV (CCTV) camera is used to image the patient and sheet during treatment. Images of captured by the camera are conveyed to the control room and viewed by the treating therapists.

In another embodiment of the invention, an analog camera is used in conjunction with a digital frame-grabber in order to transmit image data to a computer that processes and displays the images.

In a further embodiment of the invention, a method of radiation therapy quality assurance assessment is provided that includes coating a phantom with a scintillating material that conforms to the external shape of the phantom, where the phantom contains radio-opaque markers, and irradiating the coated phantom, using a therapeutic beam from a medical source of ionizing radiation, where the scintillating material emits light when exposed to the ionizing radiation, where the emitted light is collected by a digital camera, where the camera forms image data, where the image data is sent to an appropriately programmed computer, where the data is processed to determine characteristics of the beam and to determine an accuracy of machine operation for output to an operator. Quality assurance procedures for geometric QA that saves time and reduces variations that are inherent in operator dependent setup. For example, the sheet could be placed at iso-center. Images of the room lasers could then be acquired. The machine then delivers several fields of radiation at different sizes, energies and fluxes. The images acquired during each of these fields can then be analyzed to assess machine mechanical accuracy and beam characteristics such as fluence and flatness. The energy content of the beam can also be assessed by examining the relative emission of scintillator with varying amounts of transparent build-up material. This approach enables the beam energy to be determined based on the percent depth dose characteristic of the beam.

In another embodiment the system can provide information about the alignment of on-board-imaging equipment, radiation delivery and visual alignment systems (i.e. light-field or lasers). Images containing radio-opaque markers, radiation fields and visual alignment systems can be acquired. The locations of each of these elements can then be extracted and used to verify expected operation. For example, the center of the radiation field, relative to the visible radio-opaque markers, can be obtained from images of the scintillating film. The center of an image from the on-board kV imager is then measured relative to the radio-opaque markers. The differences between these two measurements indicates the deviation of the imager center from radiation center.

In another example, the image processing algorithm adjusts for the location and orientation of the phantom by extracting visible features of the phantom and determining its pose. The system then captures images of the field-light or radiation field to determine the location of the phantom relative to the LINAC. By applying geometric transformations, the system can adjust for any variations in placement of the phantom, thus overcoming variation in setup by the operator.

In another embodiment of the invention, the phantom is created such that is has large, scintillator covered faces, perpendicular to the couch top. These enable the system to acquire images of radiation fields delivered from gantry angles at or near 90 and 270 degrees.

In another embodiment of the invention the phantom is formed in the shape of a cylinder or sphere, the outer face of which is coated in the scintillating mixture. These phantoms would then be used to measure the center of rotation of a radiation therapy machine. For example, the sphere would be particularly useful when examining the performance of a robotic radiotherapy machine such as the CyberKnife.

In some embodiments of the invention, the camera may be attached to the collimator of the linear accelerator. In other embodiments it may be mounted to the room. In other embodiments it may be mounted to the couch, the gantry, or an on-board imaging detector or source.

The system tests include TG 142 daily tests for laser localization, ODI at isocenter, and collimator size indicator. TG 142 monthly tests for light/radiation field coincidence, light/radiation field coincidence (asymmetric), gantry/collimator angle indicators, jaw position indicators, jaw position indicators (asymmetric), cross-hair centering (walkout), treatment couch position indicators, and localizing lasers. TG 142 annual tests, collimator rotation isocenter, gantry rotation isocenter, coincidence of radiation and mechanical isocenter, table top sag and table angle.

One embodiment of the system QA includes using a custom phantom (see FIG. 9). Several 2.4 mm steel balls were attached to the custom phantom. Several planar faces of the phantom where then covered with a mixture of rtv-silicone and a GOS:Tb powder. This mixture was allowed to cure effectively creating a sheet of scintillator on the surfaces of the phantom.

This phantom is then placed on the treatment couch near radiation iso-center. A digital camera is attached to the head of the LINAC such that it can image the phantom. The room lights are dimmed and a predefined treatment plan in executed on the machine while images are being captured by the camera.

In order to assess Light/radiation field coincidence, laser localization, collimator size indication and jaw positioning, cross-hair centering and couch position indicator accuracy the following is performed:

The jaws are adjusted to a 5 cm×10 cm field and an image of the field light is captured at gantry angles of 0 and 90 degrees. The gantry is moved 45 degrees at which time images of the laser localization system are captured. Finally the gantry is moved to 270 degrees and delivered radiation at 6 MV and 600 MU/minute, capturing an EPID image. The gantry is then rotated to 0 degrees and MV and kV images are again acquired. Finally the gantry is moved to the 90 degree location and a kV image is acquired in the anteriorposterior direction. While the MV beam is on, the camera also captures the light emitted from the scintillating areas of the phantom. The field size is then adjusted and additional MV beams are delivered. The treatment couch is then moved by 3 cm in each of the cardinal directions and additional beams are delivered.

The captured images are processed according to the following flow: A checkerboard pattern is identified in each image. This is used to estimate the position and orientation of the phantom relative to the camera. Once this is known, the areas of the image corresponding to the planar faces of the phantom are calculated. These areas are extracted and transformed to provide images as if they had been captured from a location normal to the surface. Once this is performed, the software identifies the locations of the steel balls embedded on that surface. All images of the same surface can be aligned on the location of these balls. The software then extracts the locations of salient features such as field edges, centers and graticules from the images. The location of these features relative to one another is then calculated and reported. The software also compares the values to the prescribed tolerances and presents a pass-fail assessment.

The field edges are determined by taking the half-value of the field area and calculating the sub-pixel location of this transition. Graticule locations are determined by using a peak finding algorithm on a set of pixels orthogonal to the graticule.

In order to assess collimator and gantry rotation, as well as radiation and mechanical isocenter coincidence, a starshot is performed for each element while images are being captured. The resulting images are processed to find the center of rotation for the element that is moving.

MLC accuracy and speed can be similarly assessed by delivering a field wherein the MLCs move at prescribed rates while images are captured on the scintillating sheet. These images would include a timestamp enabling the software to calculate the location and speed of each leaf during the delivery.

Finally, a beam can be delivered while two or more axis are moving together. By capturing and analyzing several images, the accuracy of coordination could be assessed.

According to another aspect of this embodiment the intensity, energy and flatness of the radiation source can be assessed by examining the emission of light from a scintillating sheet located on a phantom. For example, a phantom under specific conditions could be calibrated such that a brightness of emission corresponds to a certain amount of dose deposition at that point. The flatness of a radiation field can be determined by examining the variation in amount of light emitted from the irradiated scintillating film. The energy content of the source can be determined by examining the amount of light emitted from different sections of a scintillating film that have differing amounts of build-up material placed between the film and the source. The change in dose deposition with depth is correlated with beam energy.

In another embodiment the invention is used to determine the accuracy of mechanical movement of a high-dose-rate (HDR) brachytherapy delivery system. This system consists of a highly radioactive seed placed at the tip of a guidewire. The guidewire is then placed in a lumen and communicated to the treatment location. In this embodiment, the lumen would be placed below or above a scintillating film. A camera would capture the emitted light and form image data that is communicated to a computer. The image data would then be processed to determine the location of the seed in each frame. The velocity, acceleration, and time at each position can then be calculated and compared with desired values. For example, the location of each dwell position is examined and compared to the desired location. The time the seed remained at each dwell position is compared to the time specified in the plan. In a further aspect of this embodiment, the strength of the source can be measured by examining the distribution of light emitted from the film. For instance examining the overall intensity of the light, or examining the distance from the center of the source at which a certain threshold (e.g. 50% of maximum) occurs.

According to another embodiment, all images were acquired with a 42 ms integration time. At this integration time a frame rate of 23 fps is achievable. Since video acquisition is not necessary (all captured images are static), images were acquired at a rate of 5 fps. In general, each set of data included of 10 images (spanning a 2 second interval). The gain on the camera was set to its minimum value.

For each data set, a set of background images was captured both before and after the acquisition. These images are averaged together to form a single background image. This image is then subtracted from each image in the dataset. Outliers are removed from the images by comparing pixel values with the median value of a neighborhood around each pixel. Pixels whose values exceed this median by more than a specified amount (threshold) are set to this median value while other pixels remain unchanged.

Signal to noise ratios were calculated by taking the average pixel intensity of an ROI within the bright region of the processed image and dividing it by the standard deviation of an ROI of the same size in a background area of the processed images.

Figure 10A:
FIGS. 10A-10D show (FIG. 10A) an unprocessed image of the light-field on the phantom with the field size 5 cm×10 cm.
Figure 10B:
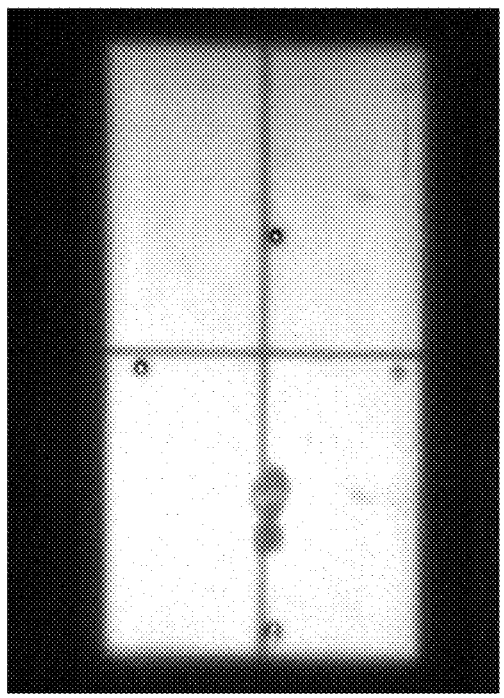
Figure 10C:
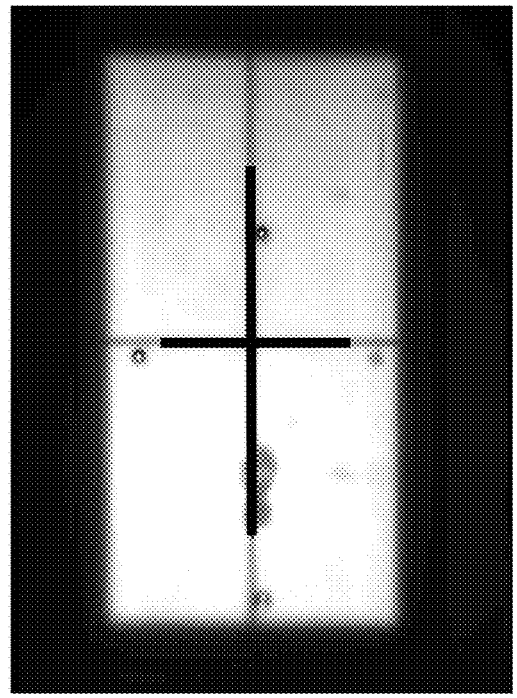
Figure 10D:
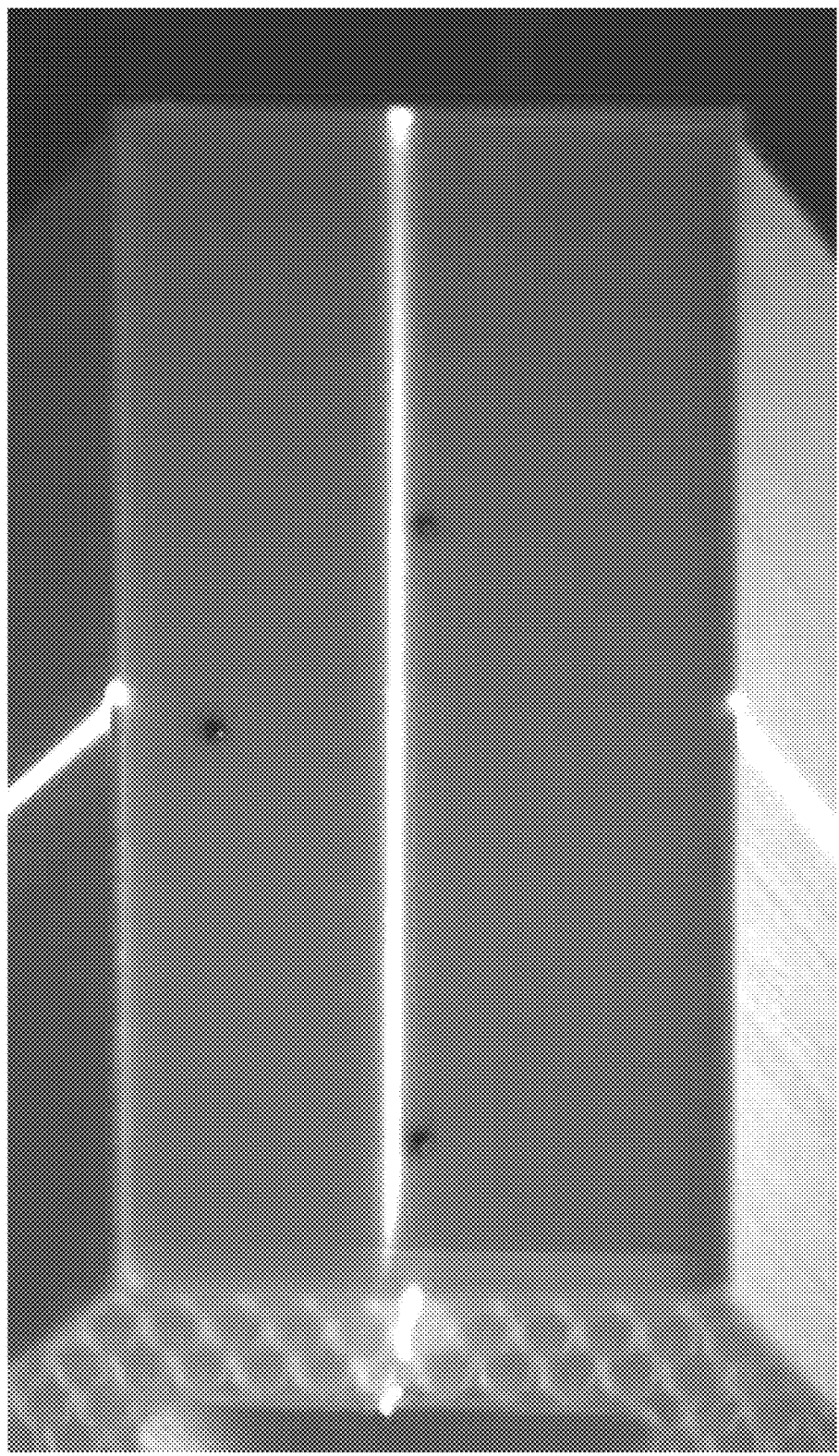

Since the camera views the field from an angle, square fields appear as a trapezoid (see FIG. 10A). In order to correct for this a projective transformation was applied. For image points on a single plane, such a transformation can be found from four points. By identifying four points in the image, and the corresponding four points in real world coordinates, transforming the imaged trapezoid into a square with known dimensions is enabled, as shown in FIGS. 10B-10D.

In yet another embodiment, images of 10×10 cm fields were imaged at different beam locations. These images were background subtracted, outliers removed and undistorted. A threshold was then applied to the image and the resulting contours (connected components) were extracted. The contours were then filtered by size to identify those that correspond to the beam profile. The outline of this contour is then fit for straight lines using a probabilistic Hough Transform. This often results in a several lines. The lines are averaged together using a weighted average where the weights are a function of the length and angular orientation of the line. This average is then reported as the location of each of the four collimators. The center of the field is calculated from the moments of all pixels within the extracted contour.

Figure 11:
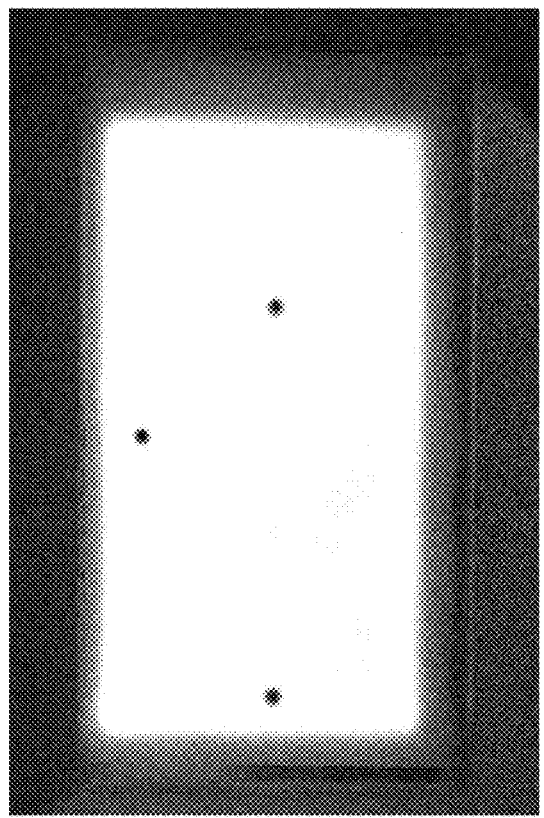
FIG. 11 shows an image of the radiation field, according to one embodiment of the invention.
Figure 12:
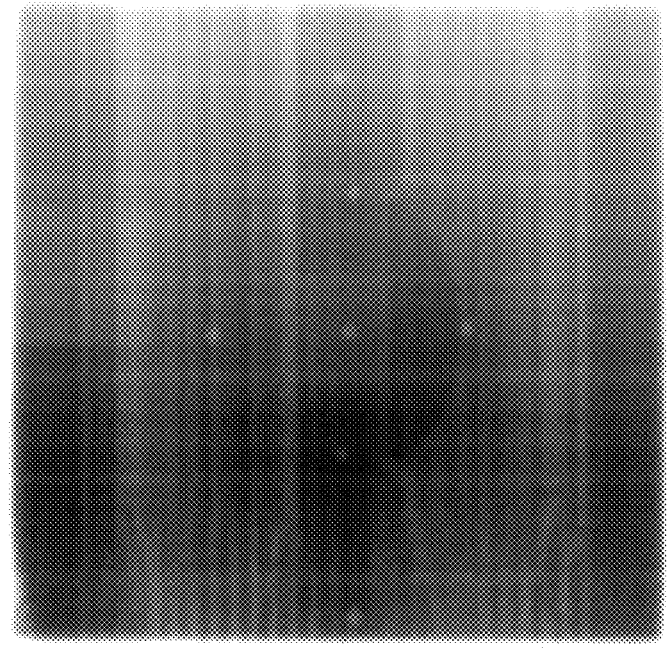
FIG. 12 shows a MV image of the phantom field size of 10 cm×10 cm, according to one embodiment of the invention.
Figure 13:
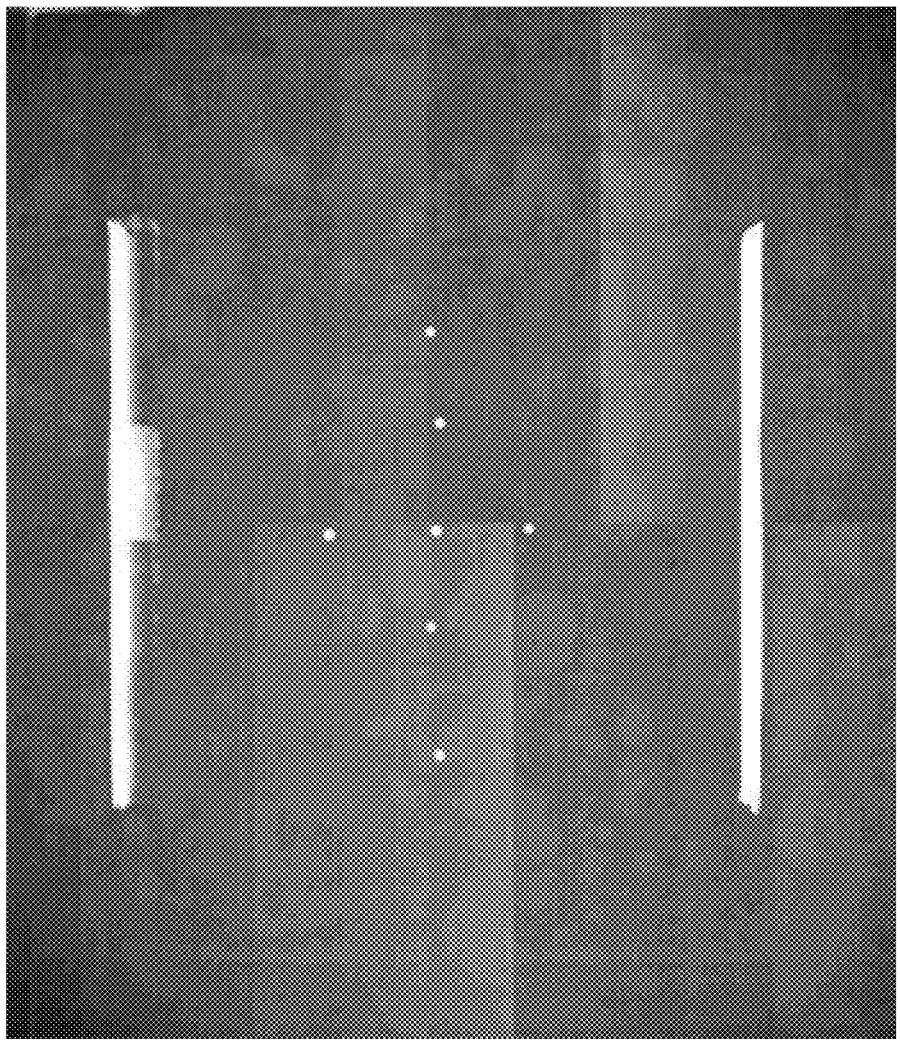
FIG. 13 shows a kV image of the phantom, according to one embodiment of the invention.
Figure 14:
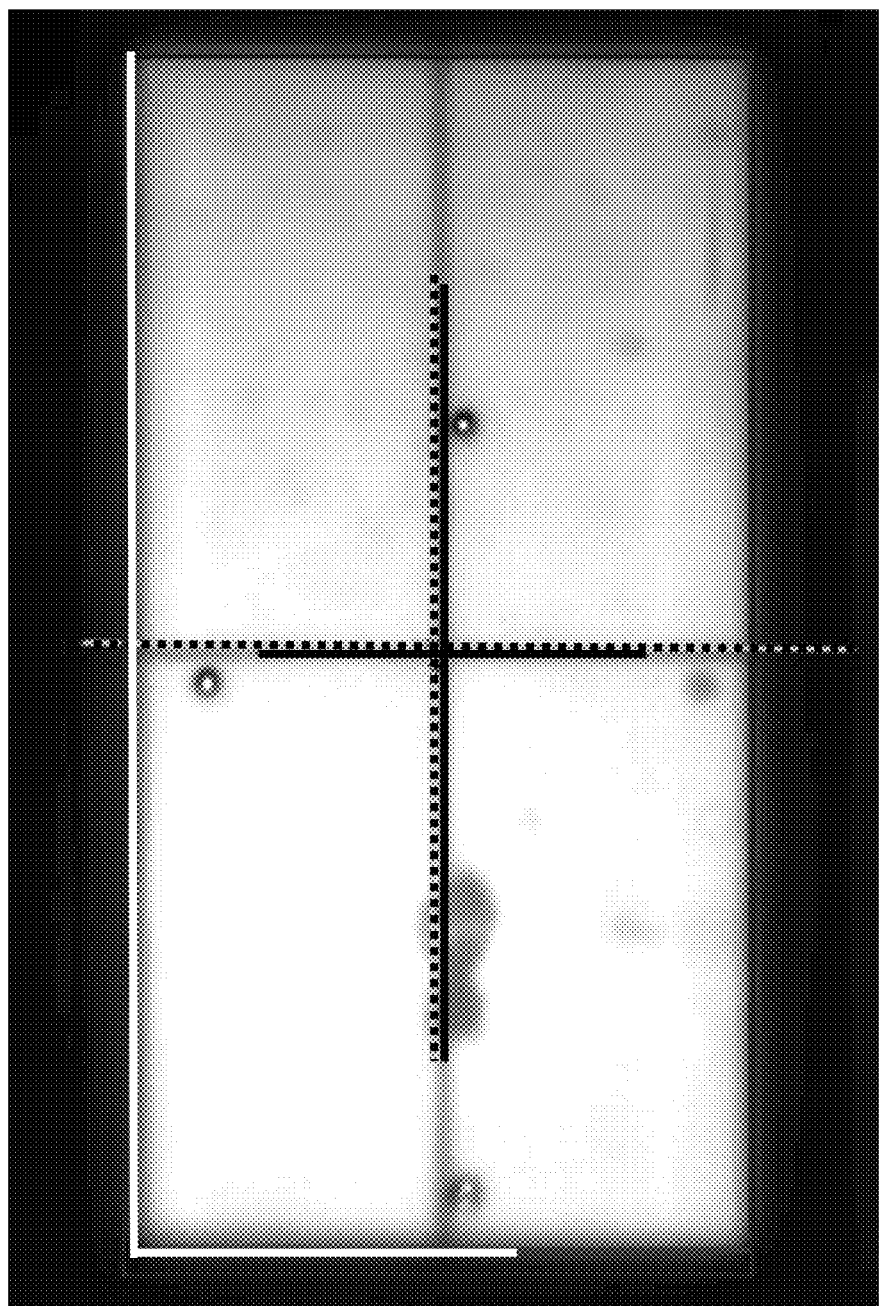
FIG. 14 shows graphical summary of the results, where the outline and center of the radiation field are shown as the image rectangle, the light field crosshairs and outline are shown in bold white lines, and the laser locations are shown in dashed lines, according to one embodiment of the invention.

FIG. 11 shows an image of the radiation field, according to one embodiment of the invention, where FIG. 12 shows a MV image of the phantom field size of 10 cm×10 cm, FIG. 13 shows a kV image of the phantom, and FIG. 14 shows graphical summary of the results, where the outline and center of the radiation field are shown as the image rectangle, the light field crosshairs and outline are shown in bold white lines, and the laser locations are shown in dashed lines, according to one embodiment of the invention.

In another embodiment, two cameras are used. A stereovision calibration and reconstruction system can then be employed to extract real-world coordinate locations of the field, where image data processing includes a 3D scene reconstruction.

In another embodiment, a depth camera is used to provide depth information for the field of view.

In another embodiment this field can be located relative to markers either on a patient or within the radiation therapy room. Examples of markers include fiducial markers placed on the patient or anatomical features. These markers can then be aligned to a planning dataset by way of registration. Once this transformation has been established the beam outline can also be transferred into the planning dataset. This enables the display of the beam profile relative to the planning data.

In another aspect of the invention, the image data is compared with treatment planning data to determine an efficacy of treatment delivery. In one aspect, the comparison of the image data includes comparing an image of the subject of interest and the beam profile with a corresponding treatment planning software image of the subject of interest and a corresponding treatment planning software image of the beam profile. In one embodiment the comparison takes the form of a correlation between pixel values between the two images. In an alternative embodiment the location of image features within the two images could be compared. In a further aspect, a relative location of the beam profile and patient anatomical landmarks are determined during data processing and compared with relative locations of corresponding elements in a treatment plan. In an example embodiment the distance between the center of the field and the patient's nose or eye could be calculated and compared with the distance predicted by the treatment planning software. In the case of breast treatment, the sheet could be used to cover a small portion of the treatment area, for example the under arm area. The distance between the couch and the field edge, or the distance between the nipple and the field edge could be calculated and compared with treatment planning data.

In yet another aspect of the invention, data presented to an observer includes a value and tolerance for the beam profile, where the beam profile includes a beam location relative to anatomical markers, beam intensity, or beam flatness. The observer includes the appropriately programmed computer, where the appropriately programmed computer determines whether calculated data is consistent with a treatment plan, where the appropriately programmed halts a treatment if a disparity is detected.

According to one aspect of the invention, the collected image data is processed to determine an efficacy of the ionizing radiation source.

In another embodiment, the processed image data is used to update the treatment plan in real time. In one such embodiment, a beam intended to treat a lung cancer lesion is delivered using a medical linear accelerator equipped with a multi-leaf collimator (MLC). The desired distance between the center of the beam and the patient's sternum is calculated. A scintillating sheet is then placed over the treatment area but not the sternum. A camera placed nearby images the sheet, and the patient's chest area. The obtained images are processed to determine the distance between the center of the beam and the sternum. The positions of the MLC are then adjusted to maintain the desired relative distance.

In one embodiment the surface of the patient may be generated from the 3D scene data. This can be registered to a surface that has been segmented from a planning CT.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example in another embodiment, several images of a field can be added together to provide an overall distribution of dose delivered during a period of time. In an alternative embodiment, the integration time of the camera is increased such that an entire treatment can be captured in a single image. This overall dose distribution is then compared with the desired distribution in order to verify that the radiation was delivered properly.

All such variations are considered to be within the scope and spirit of the present invention as defined by the following claims and their legal equivalents.

What is claimed:

1. A method of real-time radiotherapy beam visualization, comprising:
    a) disposing a free-form flexible scintillating sheet on a subject of interest;
    b) irradiating said subject of interest with a source of ionizing radiation, wherein said free-forming flexible scintillating sheet emits light when irradiated by said source of ionizing radiation;
    c) collecting said emitted light from a remote location, collecting ambient light from said remote location, or collecting emitted light from said remote location and collecting said ambient light reflected from said subject of interest from said remote location and collecting said reflected light from surrounding objects from said remote location using a camera, wherein said camera is disposed at said remote location, wherein said remote location is at a position removed from said free-forming flexible scintillating sheet, wherein said collected light is converted to image data said camera at said remote location, wherein said irradiation image data is communicated to an appropriately programmed computer, or directly to a viewing screen; and
    d) processing said irradiation image data to determine irradiation beam characteristics and characteristics of said subject of interest, using said appropriately programmed computer, wherein said irradiation beam characteristics, said characteristics of said subject of interest, or said irradiation beam characteristics and said characteristics of said subject of interest are displayed in real-time to a machine operator enabling real-time assessment of treatment delivery or storage on recordable media for later review.

2. The method according to claim 1, wherein said free-form flexible scintillating sheet comprises a scintillating powder mixed with silicone.

3. The method according to claim 2, wherein said scintillating powder comprises GdO2S:Tb or GdO2s:Eu.

4. The method according to claim 1, wherein said source of ionizing radiation comprises a medical linear accelerator or a photon beam.

5. The method according to claim 1, wherein said camera comprises a stereo-pair of said cameras, wherein said irradiation image data processing comprises a 3D scene reconstruction, or 3D localization of points within said image data.

6. The method according to claim 5, wherein said camera comprises a digital camera.

7. The method according to claim 1, wherein said irradiation image data is compared with treatment planning data to determine an efficacy of treatment delivery.

8. The method according to claim 7, wherein said comparison of said irradiation image data comprises comparing an image of said subject of interest and said irradiation beam characteristics with a corresponding treatment planning software image of said subject of interest and a corresponding treatment planning software image of said beam characteristics.

9. The method according to claim 7, wherein a relative location of said irradiation beam characteristics and patient anatomical landmarks are determined during data processing and compared with relative locations of corresponding elements in a treatment plan.

10. The method according to claim 1, wherein data presented to an observer comprises a value and tolerance for a deviation of said irradiation beam characteristics relative to values from a treatment plan, wherein said irradiation beam characteristics comprise a beam location relative to anatomical markers, irradiation beam intensity, or irradiation beam flatness.

11. The method according to claim 10, wherein said appropriately programmed computer determines whether calculated data is consistent with a treatment plan, wherein said appropriately programmed halts a treatment if a disparity is detected.

12. The method according to claim 1, wherein said collected irradiation image data is processed to determine an efficacy of said ionizing radiation source.

13. The method according to claim 1, wherein said processed irradiation image data is used to update the treatment plan in real time.

14. The method according to claim 1, wherein said processed irradiation image data is used to update a treatment plan prior to a subsequent treatment.

15. The method according to claim 1, wherein said irradiation image data is stored and may be retrieved at a future time to review treatment delivery.

16. The method according to claim 1, wherein said camera comprises a bandpass filter, wherein said bandpass filter passes an emission band of emission from said scintillating material.

17. The method according to claim 1, wherein said camera is synchronized to said source of ionizing radiation to enable acquisition of light only during a specified period of time, wherein said specified period of time corresponding to the production of said ionizing radiation or a period of time following said production of ionizing radiation.

18. The method according to claim 1, wherein said appropriately programmed computer comprises an image processing algorithm, wherein said image processing algorithm comprises the image processing steps of:
 a) background subtraction;
 b) outlier removal;
 c) calculating a contract-to-noise ratio and pixel values, wherein said contrast-to-noise ratio and said pixel values are output;
 d) transformation and cropping an image with said determined contrast-to-noise ratio and said pixel values;
 e) equalization of a histogram;
 f) applying an adaptive threshold;
 g) extracting and filtering image contours;
 h) determining Hough lines; and
 i) outputting a field center calculation and determined average lines of a collimator location.

19. A method of radiation therapy quality assurance assessment comprising:
 a) coating a phantom with a scintillating material that conforms to the external shape of said phantom; and
 b) irradiating said coated phantom, using a therapeutic beam from a medical source of ionizing radiation, wherein said scintillating material emits light when exposed to said source of ionizing radiation, wherein said emitted light is collected by a camera at a remote location, wherein the camera forms irradiation image data, wherein said irradiation image data is sent to an appropriately programmed computer, wherein said irradiation image data is processed to determine characteristics of said irradiation beam and to determine an accuracy of machine operation assessment of treatment delivery for output to an operator.

20. The method of radiation therapy quality assurance assessment of claim 19, wherein said collected irradiation image data is used to determine acceleration, velocity, accuracy and repeatability of mechanical motions of said source of ionizing radiation.

21. The method of radiation therapy quality assurance assessment of claim 20 wherein said medical source of ionizing radiation comprises a linear accelerator wherein said mechanical motions are selected from the group consisting of motions of the gantry, collimator, collimators, source and couch.

22. The method of radiation therapy quality assurance assessment of claim 20 wherein said source of radiation comprises a radioactive seed at a tip of a guidewire, wherein said guidewire is placed in a lumen and communicated to a treatment location, wherein said lumen is placed proximal to said scintillating material, wherein said irradiation image data is processed to determine a location of said radioactive seed within each frame of said image data, wherein a velocity, an acceleration, and a time at each position is calculated and compared with desired values, wherein a strength of said source of ionizing radiation is measured by examining a distribution of light emitted from the said scintillating material.

23. The method of radiation therapy quality assurance assessment of claim 19, wherein said collected irradiation image data is used to determine radiation source properties selected from the group consisting of fluence, flatness, and energy.

24. The method of radiation therapy quality assurance assessment of claim 19, wherein said phantom contains radio-opaque markers, and wherein said images of said radio-opaque markers are formed using a medical imaging system, wherein the alignment of the radiation source to the medical imaging system is assessed by processing of said images.

* * * * *